United States Patent [19]

Pirmantgen

[11] Patent Number: 4,655,201

[45] Date of Patent: Apr. 7, 1987

[54] KNEE ORTHOSIS AND JOINT CONSTRUCTION THEREFOR

[75] Inventor: Robert E. Pirmantgen, Chicago, Ill.

[73] Assignee: Northwestern University, Evanston, Ill.

[21] Appl. No.: 630,648

[22] Filed: Jul. 13, 1984

[51] Int. Cl.⁴ ............................................. A61F 3/00
[52] U.S. Cl. ...................................... 128/80 C; 623/39
[58] Field of Search ................ 128/80 C, 80 F, 80 R, 128/88; 3/22, 26; 623/39, 43

[56] References Cited

U.S. PATENT DOCUMENTS

| | | | |
|---|---|---|---|
| 1,390,915 | 9/1921 | Loth | 3/22 |
| 1,851,241 | 3/1932 | Dresser | 128/80 F X |
| 2,410,560 | 11/1946 | Witte | 128/80 F X |
| 2,433,571 | 12/1947 | Markkula | 128/80 F |
| 2,516,253 | 7/1950 | Pieterick | 128/80 F |
| 3,779,654 | 12/1973 | Horne | 128/80 F X |
| 3,817,244 | 9/1974 | Taylor | 128/80 C |
| 3,902,482 | 2/1975 | Taylor | 128/80 F |
| 4,241,730 | 1/1980 | Helfet | 128/80 C |
| 4,320,747 | 3/1982 | Daniell, Jr. | 128/80 C |
| 4,361,142 | 11/1982 | Lewis et al. | 128/88 X |
| 4,379,463 | 4/1983 | Meier et al. | 128/80 C |
| 4,463,751 | 8/1984 | Bledsoe | 128/80 C |

FOREIGN PATENT DOCUMENTS

| | | | |
|---|---|---|---|
| 473487 | 3/1929 | Fed. Rep. of Germany | 3/22 |
| 826333 | 12/1951 | Fed. Rep. of Germany | 3/22 |
| 1564905 | 4/1980 | United Kingdom | 3/22 |

OTHER PUBLICATIONS

Orthopaedic Appliances Atlas, pp. 381-382, (The American Academy of Orthopedic Surgeons, 1952).

Primary Examiner—Clifford D. Crowder
Attorney, Agent, or Firm—Tilton, Fallon, Lungmus

[57] ABSTRACT

An orthotic joint, and the orthosis with which it is used, for the protective treatment of ligamentous injuries or deficiencies, or as a supplement to total joint replacement. The joint includes a tibial member defining a narrow, upwardly-opening socket and a femoral member having a planar head portion slidably received within that socket. Therefore, on each side of the head portion are a pair of opposing and slidably engaging surfaces, one provided by the head portion and the other by the side wall of the socket. One of those opposing surfaces is provided with a recess having its major dimensions extending in the plane of that surface and having a narrow cam track about its periphery; the other of the opposing surfaces being provided with at least one protuberance engageable with portions of that narrow cam track during flexion and extension for exerting constraining forces similar to those that would be exerted by selected ligaments of a patient's knee if such ligaments were present, healthy, and functioning properly.

7 Claims, 27 Drawing Figures

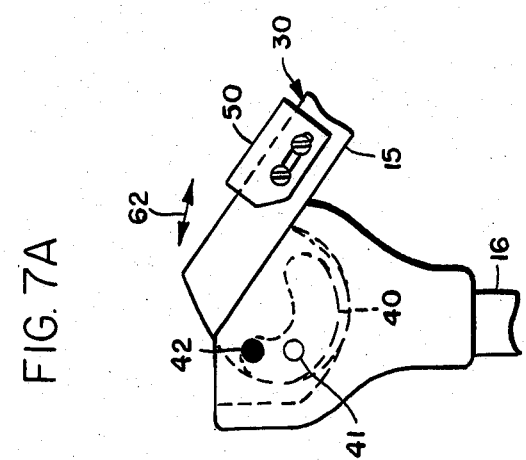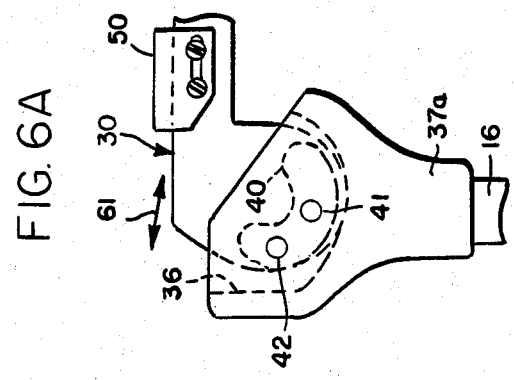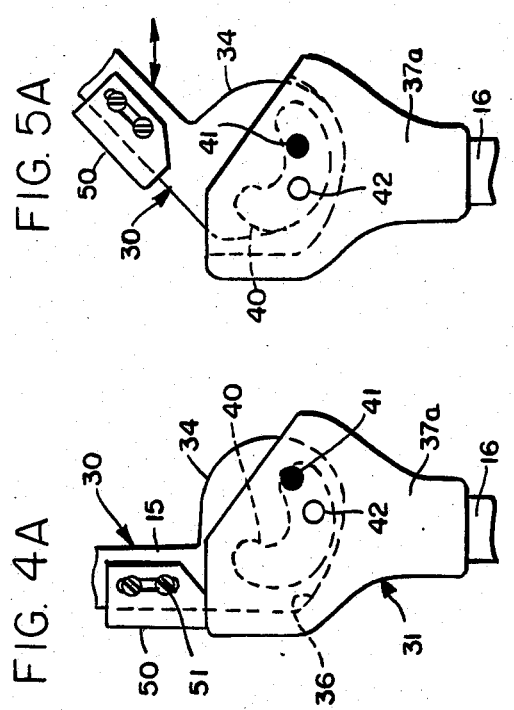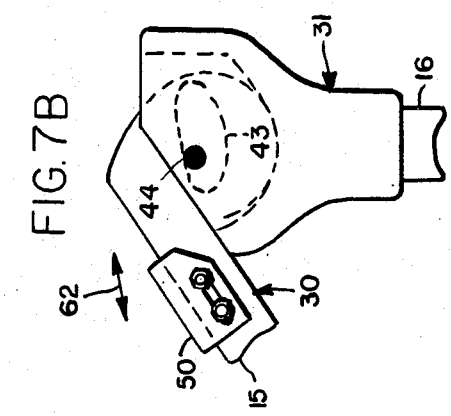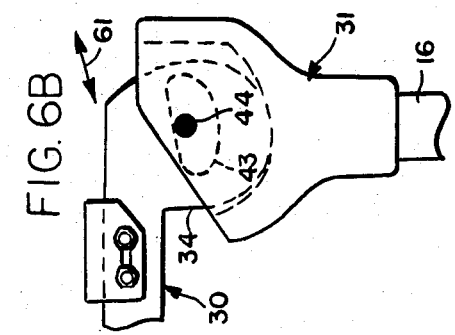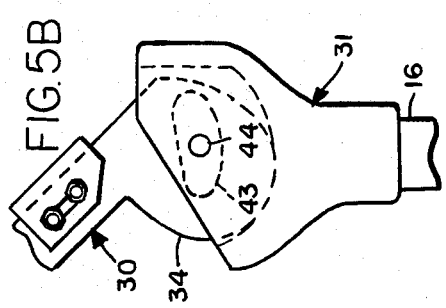

FIG. 8
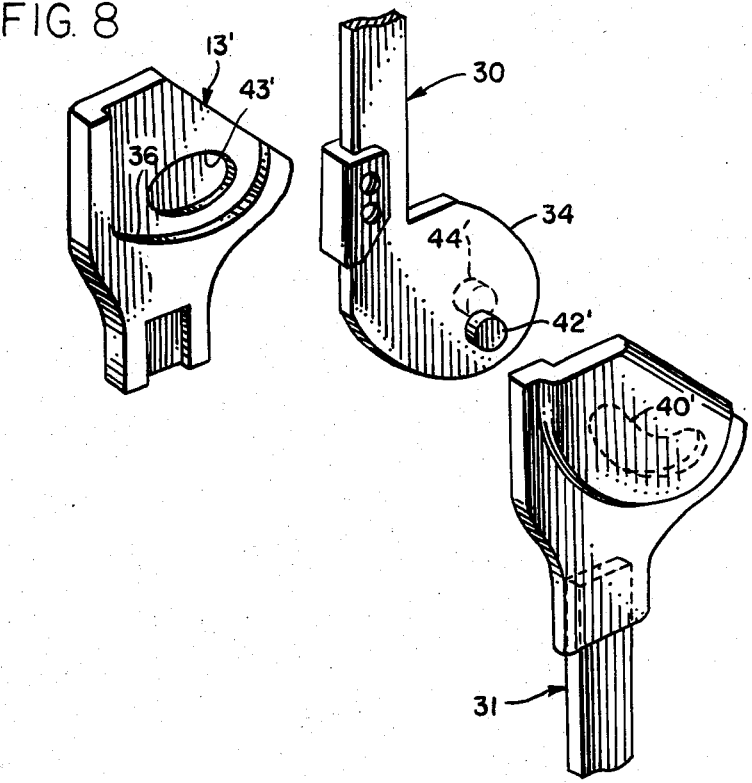
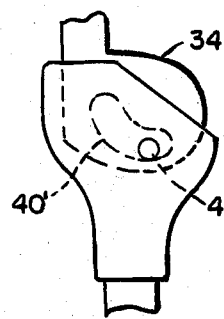
FIG. 9A
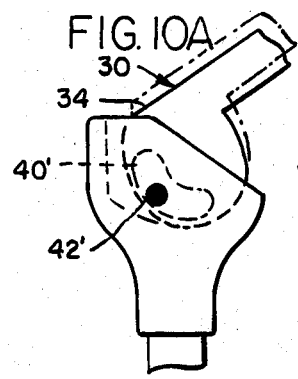
FIG. 10A
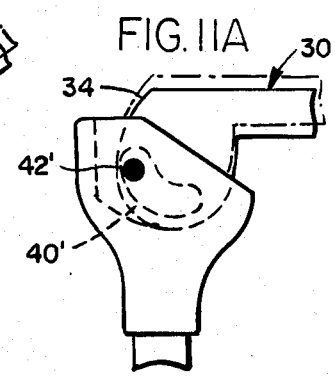
FIG. 11A
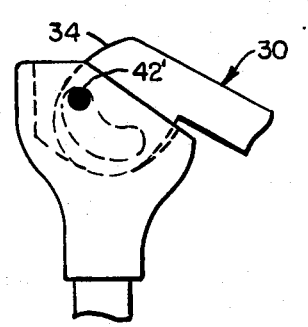
FIG. 12A
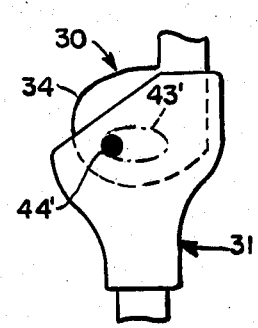
FIG. 9B
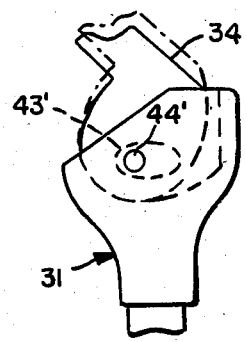
FIG. 10B
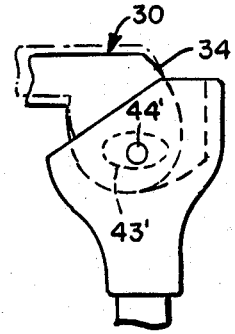
FIG. 11B
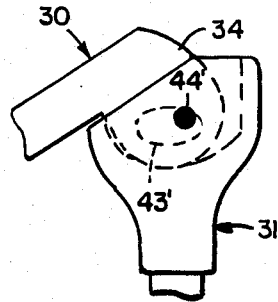
FIG. 12B

KNEE ORTHOSIS AND JOINT CONSTRUCTION THEREFOR

BACKGROUND

U.S. Pat. No. 4,361,142 discloses a knee orthosis having a pair of knee joint assemblies 13 and 14 positioned on opposite sides of a patient's knee, each assembly having a femoral sidebar 15 and a tibial sidebar 16 extending alongside the upper and lower leg, respectively. The upper femoral sidebars are held along the upper leg by suspension means in the form of interfacial member 17, straps 20, 21, and pad 26 and, similarly, the lower tibial sidebars are immobilized along opposite sides of the lower leg by suspension elements in the form of interfacial members 18 and 19 and straps 22-24.

At the upper end of each tibial sidebar is a body portion 40 having a pair of planar side walls spaced apart to define a narrow upwardly-opening socket 38 that slidably receives the head portion 34 of a femoral member 30 of which the upper femoral sidebar 15 is an integral part (FIG. 2). Within the socket is a narrow arcuate guide surface 39 that engages the bearing surface 35 of the femoral member for guiding movement of the members between flexion and extension along constantly changing instantaneous axes of rotation. When the joint is in flexion as shown in FIG. 8, the head 34 would be capable of limited sliding movement posteriorly and anteriorly along the guide surface 39 in the absence of some additional constraining force. The interfitting relationship therefore assures stability at all degrees of flexion but there is nevertheless sufficient laxity in the mechanical joint to permit normal action of the patient's knee. Healthy ligaments are allowed to control natural knee movement. At the same time, at least one flexible but non-stretchable strap 33, and ordinarily a plurality of such straps (three are shown in FIG. 2), secured at selected points to the respective members of the orthotic joint, perform essential functions that would normally be performed by the injured or chronically deficient ligament, thereby protecting that ligament without interfering with the functions of the healthy ligaments. The positions and connections of the straps depend on the ligament or ligaments requiring protection or the stability required if such ligament or ligaments are absent. In any case, for any grouping of straps there is a sequential tensioning and untensioning of such straps during flexion and extension, with the result that the injured or deficient ligament is protected at all degrees of flexion.

The arrangement and positioning of straps 33 depend on the particular ligament or ligaments requiring protection. FIGS. 1-8 illustrate the attachment and positioning of straps for a patient with injury to or chronic deficiency of the posterior cruciate ligament. A primary function of that ligament in a normal knee joint is to pull the head of the femur in a posterior or rearward direction over the tibial articular surface during flexion and to hold it in a rearward position when the knee is fully flexed. The articulation of the femoral member 30 and tibial member 31 of the orthotic joint mimics the articulation of the natural joint, and the set of straps 33 is mounted to exert forces during flexion, as well as at extension and 90° flexion, that mimic forces that would normally be exerted by a natural posterior cruciate ligament. For a patient whose condition requires protection of other major ligaments, the straps and their points of attachment would be different. For example, FIG. 9 depicts an orthotic joint for use with a patient having an injured or chronically deficient anterior cruciate ligament, and FIG. 10 illustrates a joint with strap attachment points arranged for protection of a collateral ligament.

While the orthosis briefly described above and disclosed in detail in U.S. Pat. No. 4,361,142 is considered superior to previous orthoses because, among other things, there is sufficient laxity in the mechanical joint to permit healthy ligaments to control natural knee movement, proper operation of the orthotic joint in protecting the injured or deficient ligaments requires precise adjustment of the length and location of attachment of the straps 33. Slight stretching of the straps over a period of extended use reduces the protective function of the orthosis. While problems of stretching might be reduced by forming the straps or cables of metal (as indicated in the patent), the constant flexing and tensioning of those straps or cables may nevertheless produce dimensional changes that require periodic inspection and possible adjustment or replacement. Wear on those straps or cables, and their points of connection is inevitable, especially in view of the exposed condition of those elements. Also, because the straps are exposed and bulge outwardly when they are untensioned, such straps are vulnerable to contact with objects or clothing that might interfere with their proper operation.

SUMMARY OF THE INVENTION

This invention is therefore concerned with a knee orthosis, and the joint construction for such an orthosis, which achieves the advantages of the structure disclosed in U.S. Pat. No. 4,361,142 without the disadvantages described above. Specifically, this invention is directed to an orthotic joint (and the orthosis with which it is used) which provides sufficient laxity so that it does not constrain normal movements of a patient's knee but nevertheless is capable of restraining abnormal knee movements (or, in the case of prosthetic joint replacement, preventing movements that do not conform with the prescribed action of the replacement joint) without the use of external flexible straps or cables.

As in the patented construction, the joint assembly includes a rigid planar femoral member having a head portion with a narrow arcuate bearing surface of varying radii of curvature and having a femoral sidebar projecting from that head portion and adapted to extend upwardly alongside a wearer's upper leg. The assembly also includes a rigid tibial member having a body portion and a tibial sidebar adapted to extend downwardly alongside a wearer's lower leg. The body portion has a pair of planar side walls spaced apart to define a narrow upwardly-opening socket that slidably receives the head portion of the femoral member. The socket includes an arcuate guide surface that is engagable with the bearing surface of the femoral member for guiding movement of the two members between flexion and extension along constantly changing instantaneous axes of rotation.

In the joint assembly of this invention, the head portion has planar surfaces on its opposite sides that slidably engage the side walls of the body portion within the socket; therefore, on each side of the head portion there are presented a pair of opposing and slidably engaging surfaces, one provided by the head portion and the other by the body portion. One of those surfaces of each pair is provided with a recess that has its major dimensions extending along the plane of such surface and having a narrow cam surface or track extending about the periphery of the recess. The outer of the opposing surfaces of each pair is provided with at least one protuberance engagable with portions of the narrow cam track of the opposing surface during at least a portion of the full range of travel between flexion and extension for exerting constraining forces similar to those that would be exerted by certain ligaments of the wearer's knee if such ligaments were healthy and functioning properly. The protuberances, cam tracks, and recesses are dimensioned and shaped to permit a laxity or play in the orthotic joint that allows the healthy ligaments of the knee, those that are not being protected by the orthosis, to function in their normal manner without interference by the orthosis.

The orthosis also includes adjustable stop means for limiting the degree of extension of the orthotic joint and, hence, the degree of extension of the wearer's leg. Adjustment of the stop not only permit the orthosis to be adjusted to meet the specific needs of a patient but also allows progressive re-setting of the stop as healing occurs following injury or surgery.

Other features, advantages, and objects will become apparent from the specification and drawings.

DRAWINGS

FIGS. 4A and 4B are schematic elevational views of opposite sides of the joint of FIG. 3 with the members thereof in full extension.

FIGS. 5A and 5B are similar to FIGS. 4A and 4B but depict the femoral member at approximaly 45° flexion.

FIGS. 6A and 6B show the femoral member at approximately 90° flexion.

FIGS. 7A and 7B show the femoral member at maximum flexion.

FIG. 8 is an exploded perspective view of an orthotic joint embodying the invention and constructed for treatment of injury to or deficiency of the posterior cruciate ligament.

FIGS. 9A and 9B are schematic or diagramatic elevational views showing the joint of FIG. 8, viewed from opposite sides, in full extension.

FIGS. 10A and 10B show the same joint at 45° flexion.

FIGS. 11A and 11B at 90° flexion.

FIGS. 12A and 12B at maximum flexion.

Figure 13:
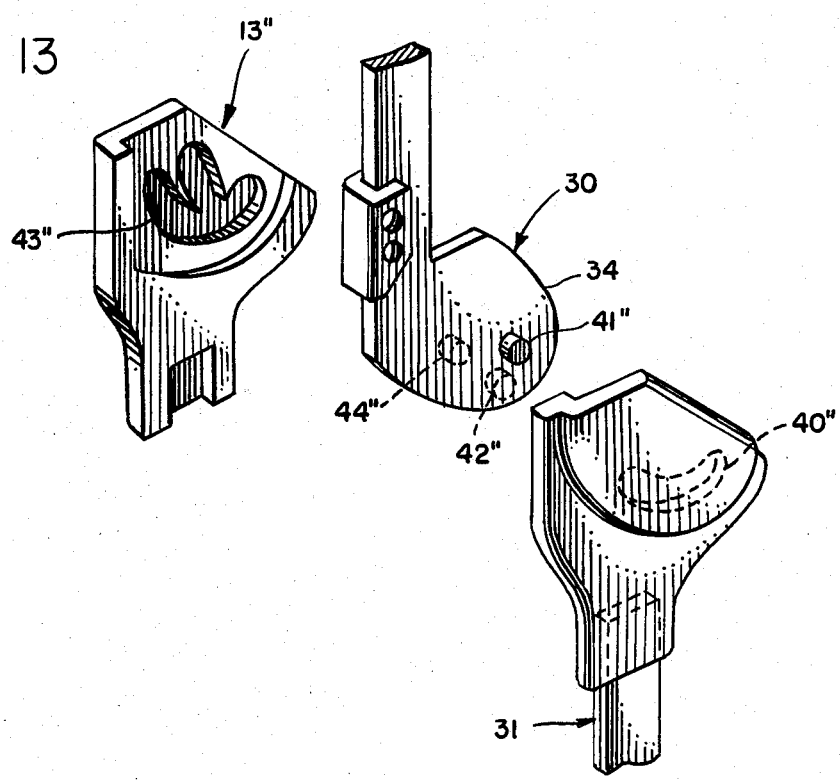

FIG. 13 is an exploded perspective view of an orthotic joint constructed for treating injury to or deficiency of the anterior cruciate ligament.

Figure 14A:
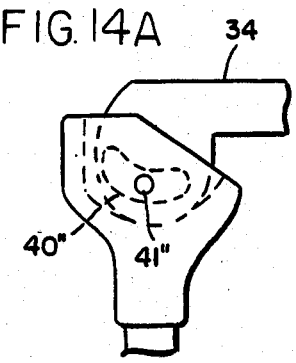
Figure 14B:
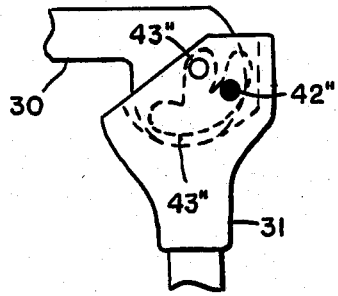

FIGS. 14A and 14B are schematic elevational views of opposite sides of the joint of FIG. 13 showing the members at approximately 90° flexion.

Figure 15A:
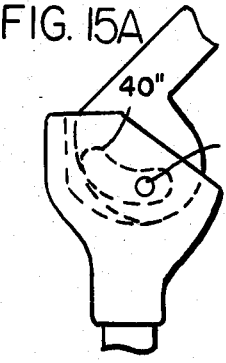
Figure 15B:
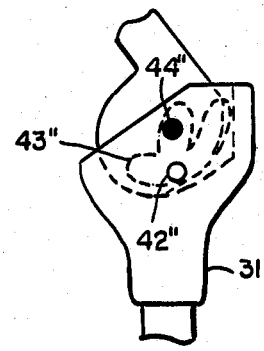

FIGS. 15A and 15B illustrate the same joint at approximately 45° flexion.

Figure 16A:
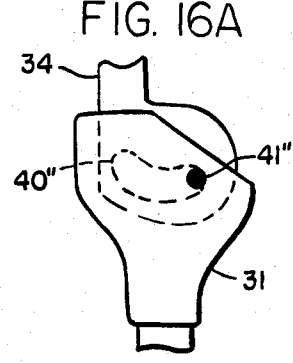
Figure 16B:
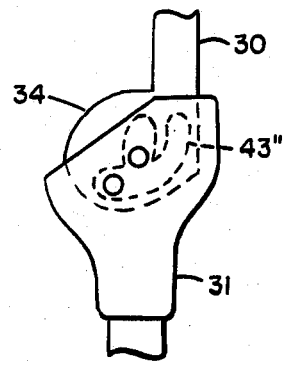

FIGS. 16A and 16B depict the members at full extension.

DETAILED DESCRIPTION

Figure 2:
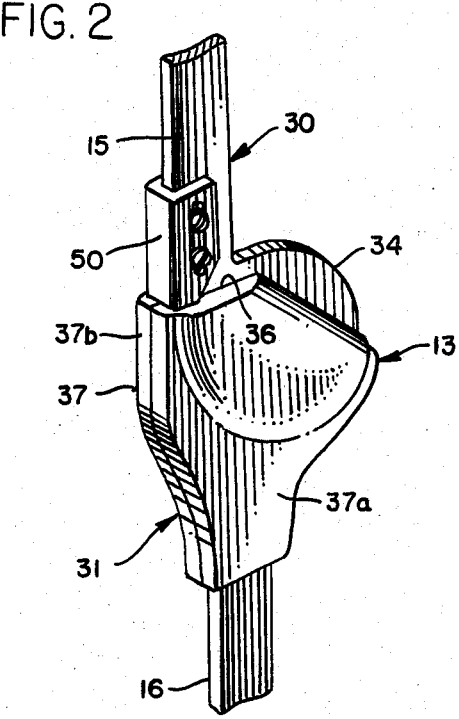
FIG. 2 is a perspective view of one of the orthotic joints of that orthosis.
Figure 1:
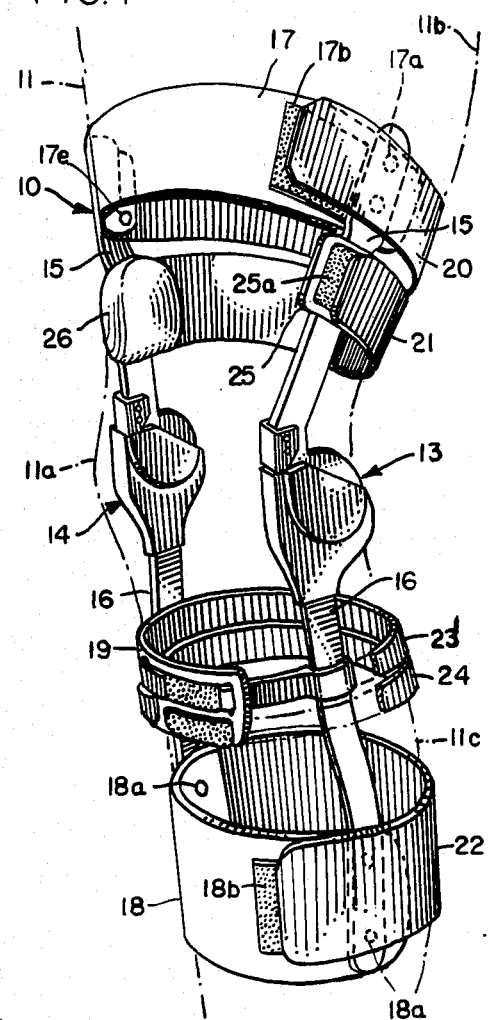
FIG. 1 is a perspective view of a knee orthosis embodying the present invention.

Referring to FIG. 1, the numeral 10 generally designates a knee orthosis embodying the invention, the orthosis being shown as it might be worn on the left leg 11 of a patient. The orthosis consists essentially of a pair of knee joint assemblies 13 and 14 positioned on opposite sides of the patient's knee 11a, each assembly having sidebars 15 and 16 extending alonside the upper leg 11b and lower 11c, respectively, and means for holding the assemblies in such positions. In the embodiment illustrated, such means takes the form of rigid or semi-rigid interfacial members or plates 17, 18, and 19, and suspension members or straps 20, 21, 22, 23, and 24. The upper or proximal plate 17 is shaped to conform to the contour of the anterior upper leg 11b and is securely connected to the upper ends of femoral sidebars 15 by means of rivets 17a or any other suitable connecting means. The suspension strap 20 is permanently joined at one end to one of the sidebars (or to one end of plate 17) and is detachably connected at its other end to the other sidebar or to the outer surface of plate 17 adjacent to the other sidebar. Such releasable attachment may be achieved by securing Velcro patches 17b to the overlapping portions of strap 20 and interfacial member or plate 17.

Suspension strap 21 is similarly secured to the femoral sidebars 15 of the orthosis. One of the sidebars may be equipped with an extension plate 25 that may, if desired, be enlarged to extend across the anterior upper leg 11b to the other femoral sidebar, and a resilient medial pad or cushion 26 may be secured to the opposite sidebar for the purpose of achieving proper positioning and fit of the orthosis and to increase wearer comfort. The suspension strap 21 works in conjunction with cushion 26 and extension plate 25 to help immobilize the femoral sidebars 15 of the orthosis with respect to the femur, thereby complementing interfacial member 17 and suspension strap 20. In that connection, reference may be had to co-pending co-owned application Ser. No. 630,649, filed July 13, 1984, now U.S. Pat. No. 4,565,190 for the details of what are believed to be improvements in femoral suspension construction.

The lower or distal interfacial member or plate 18 is shaped to conform to the contour of the anterior lower leg and is similarly secured to the distal ends of tibial sidebars 16 by rivets 18a. Such rivets also permanently join one end of the suspension strap 22 to one of the sidebars 16, and Velcro patches 18b releasably join the opposite end of the strap to rigid member 18. The purpose of the interfacial members and straps is to immobilize the femoral and tibial sidebars in relation to the upper and lower leg of the wearer, and to maintain the orthotic joints in proper alignment with the wearer's knee. To achieve those objectives, various modifications or alterations may be made in the suspension system and different means for immobilizing the sidebars and for locating the joint assemblies might be provided. For example, the sidebars 15 and 16 might be embedded in plaster casts formed about the wearer's leg above and below the knee, as in the case where near-anatomical joint motion is needed to prevent knee damage while a patient recovers from a femoral fracture. Since the present invention is not concerned with the construction of the suspension system or with any specific means for achieving immobilization of the femoral and tibial sidebars and the joint assemblies of the orthosis, further detailed description of such suspension means is believed unnecessary herein.

The joint assemblies 13 and 14 on opposite sides of the wearer's leg are basically the same in construction, the main differences being that they are reverse or mirror images of each other with the sidebars 15 and 16 of somewhat different length and configuration to follow the differences in contour of the wearer's leg. There may also be differences in the recess and protuberance construction (as described hereinafter) between the hinge assemblies on opposite sides of the knee depending on the particular ligamentous injury being treated although, in general such arrangements would ordinarily be the same. While the details of the left assembly 13 are shown in the drawings, and are described hereinafter, such detailed disclosure should be understood as also being applicable to the right assembly 14.

Each orthotic joint assembly includes two basic components: a femoral member 30 and a tibial member 31. The femoral member 30 is planar and includes, as an integral portion thereof, the upstanding elongated femoral sidebar 15. In addition, the femoral member has at its lower end an enlarged planar head portion 34. The head portion has an arcuate bearing surface 35 of varying radii of curvature with the posterior portion 35a of that surface having smaller radii of curvature than the distal portion 35b thereof. In general, the curvature of bearing surface 35 simulates or conforms to the curvature of a femoral condyle viewed in sagittal section. It will be noted, however, that the leading or anterior portion 35c of the bearing surface is substantially straight and constitutes an extension of the leading edge of femoral sidebar 15. While the femoral member 30 may be formed of any strong, rigid, and durable material, it is believed that a lightweight metal such as aluminum is particularly effective.

Figure 3:
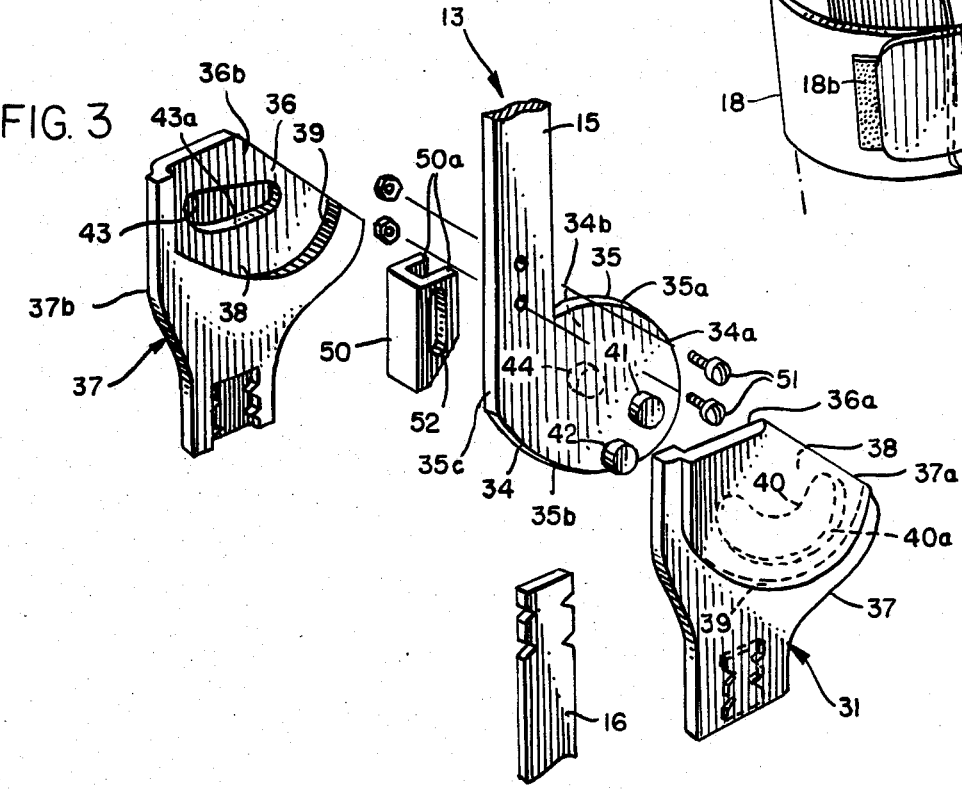
FIG. 3 is an exploded perspective view of an orthotic joint of the type shown in FIG. 2 with the components of such joint constructed for treatment of a patient with injury to or deficiency of the collateral ligaments.

The head portion 34 of the femoral member is received with an upwardly-facing socket 36 provided by body portion 37 of tibial member 31. The tibial member includes both the socket-providing body portion 37 and the depending tibial sidebar 16. The two portions may be formed integrally of the same rigid material although it is believed preferable to fabricate body portion 37 from a rigid polymeric material such as polypropylene or a polypropylene-polyethylene copolymer (90/10% formulation has been found effective) and to embed the upper end of the tibial sidebar 16, formed of aluminum or other material having similar properties, within the body portion as indicated. The body portion 37 is shown to be formed in two sections, namely, a lateral section 37a and a medial section 37b. Ideally, socket 36 is formed by molding, casting, or machining the two sections so that the lateral section 37a of the body portion defines one half 36a of socket 36, and the other section 37b defines the other half 36b of the socket (FIG. 3); however, if desired, the socket may be molded or otherwise formed entirely in one of the sections. In any event, the body portion 37 includes a pair of opposing, parallel, planar side wall surfaces 38 that, together with a narrow arcuate guide surface 39 (provided jointly by the two sections 37a and 37b), define socket 36. The guide surface 39, when viewed in outline, corresponds closely to the curvature of bearing surface 35 of femoral member 30. Maximum contact between such surfaces occurs when the members are in extension (FIGS. 4A and 4B). In that condition of close conformity, with the substantially straight leading surface 35c of the femoral head portion abutting the substantially straight anterior portion of the guide surface 39, the femoral and tibial members are restrained against both hyperextension and posterior-anterior sliding translation. Because the curvature of the posterior portion 35a of the arcuate femoral bearing surface 35 is of smaller radii than the distal portion 35b thereof, the extent of contact between bearing surface 35 and guide surface 39 decreases during flexion (FIGS. 5A, 5B, 6A, 6B, 7A, 7B). As the degree of flexion increases, the more limited contact between the bearing and guiding surfaces, and the decreased anterior-posterior dimension of the head portion 34 in relation to that of socket 36, allows limited anterior-posterior sliding movement of the head portion within the socket, at least in the absence of some natural or artificial constraining means. Thus, referring to FIGS. 5A through 7B, in the absence of some constraining means, head portion 34 would be free to slide anteriorly a limited distance within socket 36 until its curved distal surface engages the straight anterior surface of the socket.

The sections 37a and 37b of the body portion 37 are fused or otherwise permanently joined together in the finished product. The spacing between the opposing faces 36a and 36b of the socket is the same as, or only slightly greater than the distance between the lateral and medial planar surfaces 34a and 34b of head portion 34 of the femoral member. Therefore, when the parts are assembled, a coplanar relationship is maintained with the planar surfaces on opposite sides of the head portion 34 being in sliding engagement with the planar surfaces 38 within the socket. Stated differently, in the assembled joint there are a pair of opposing and slidably-engagable surfaces along each side of the head portion, one pair constituting lateral surface 34a of the head portion and inner surface 38 of section 37a of the body portion, and the other pair comprising medial surface 34b of the head portion and surface 38 of the medial section 37b of the body portion 37.

An arcuate or crescent-shaped recess 40 is formed in socket-defining surface 38 of the lateral section 37a of the tibial body portion 37. The shape of the recess is developed to perform a camming function, and a narrow cam surface or track 40a defines the periphery of that recess. It will be observed that the major dimensions of the recess extend in a plane parallel with surface 38. Recess 40 receives protuberances 41 and 42 projecting laterally from the head portion of femoral member 30. Two such protuberances are shown for clarity of illustration and ease of manufacture, but it should be understood that such protuberances may be merged together to form a single protuberance having portions capable of making sequential contact with cam track 40a during flexion and extension in the manner hereinafter described.

A similar recess 43, but of different shape, is formed in the surface 38 of the medial section 37b of the body portion 37. Like recess 40, recess 43 has its greatest dimensions extending in the plane of surface 38 and has its periphery defined by a narrow bearing surface or track 43a. That track is engagable with one or more medial protuberances 44 projecting medially from surface 34b of the head portion 34 of the femoral member.

An adjustable stop member 50 is mounted upon femoral member 30 just proximal to head portion 34. The stop member is generally U-shaped when viewed in horizontal section and has side portions 50a that engage the lateral and medial surfaces of the femoral sidebar 15 just proximal to head portion 34. Screws or bolts 51 extend through slots 52 and openings 53 and may be tightened to clamp the side walls 50a into tight locking engagement with the lateral and medial surfaces of sidebar 15.

The operation of the joint assembly is somewhat schematically depicted in FIGS. 4A through 7B with figures bearing the same numerals but different letters showing the assembly from opposite sides under the same condition of flexion. Thus, FIGS. 4A and 4B illustrate the assembly from opposite sides under a condition of full extension, and FIGS. 7A and 7B show the same assembly under a condition of maximum flexion. Only the recesses and protuberances facing the viewer are shown in each view with the protuberance that is operative at each of the illustrated degrees of flexion being fully shaded and the non-operative protuberance(s) being depicted in solid lines (for clarity of illustration) but unshaded.

The orthotic joint assembly of FIGS. 3 through 7B is intended for use by a patient having injury to or deficiency of the collateral ligaments. In a normal knee joint, the collateral ligaments function primarily to prevent vertical separation (i.e., proximal-distal separation or superior-inferior separation) between the femoral and tibial components, and they do so without at the same time preventing limited anterior-posterior displacement of such components as the leg is flexed. Anterior-posterior travel of the head of the femur in relation to the condyles of the tibia is controlled largely by the anterior and posterior cruciate ligaments. The orthotic joint of FIGS. 3–7B protects abnormal operation of the knee joint that might result from a deficiency of the patient's collateral ligaments caused by injury, surgery, or other possible reasons, without interfering with normal operation of the patient's healthy cruciate ligaments. Natural action of the knee joint is therefore permitted, the function of the orthosis being to reinforce or protect the knee against abnormal operation because of the deficient (or possibly absent) collateral ligaments.

In a condition for full extension, the head portion 34 of the femoral member 30 is seated within socket 36 with its bearing surfaces fully engaging the corresponding guide surfaces defining that socket. Vertical separation between the elements of the orthotic joint is prevented because of engagement between protuberance 41 and (an upper portion of the cam track) at the extreme right end of recess 40 as viewed in FIG. 4A. Protuberance 41 is shaded in that figure to indicate that of the three protuberances 41, 42, and 44, it is the only one that functions at that moment to prevent such separation. It will be observed in FIGS. 4A and 4B that protuberances 42 and 44 do not engage portions of the cam tracks of the recesses in which they are disposed; therefore, if it were not for protuberance 41, the femoral member 30 could be shifted upwardly a limited extent with respect to tibial member 31.

In a condition of partial flexure of the orthotic joint, specifically, with the femoral member at an angle of about 45° from the vertical, protuberance 41 remains in engagement with the upper cam track of recess 40 and continues to prevent relative upward displacement of the femoral member 30. However, neither it nor the other protuberances 42, 44 prevent limited anterior-posterior movement of the femoral member 30 in relation to socket 36. Such movement of the femoral member is also possible at 90° flexion (FIGS. 6A, 6B) as indicated by arrow 61, and even when the joint is fully flexed as represented by arrow 62 (FIGS. 7A, 7B).

However, when the joint is at about 90° flexion, protuberance 44 and the upper cam track of recess 43 become operative to prevent vertical movement of the femoral head 34 within its socket 36. The narrow upper cam track of recess 43 serves to guide the head should anterior-posterior forces be exerted in the direction of arrow 61. When the joint is fully flexed (FIGS. 7A, 7B), protuberance 44 and the upper cam track of recess 43 remain operative, and protuberance 42 and the cam track of recess 40 become operative, to prevent relative superior movement of the femoral head without at the same time preventing limited anterior-posterior movement.

Since the orthotic joint does not prevent limited relatively anterior-posterior movement of the femoral head within its socket when the joint is in any stage of partial to complete flexure (FIGS. 5A through 7B), and since such movement of the natural joint is controlled by the cruciate ligaments, the patient's cruciate ligaments are allowed to function normally without being constrained by the orthotic joint. The orthotic joint of FIGS. 3–7B mimics only those forces that would normally be exerted by normal, healthy collateral ligaments. Therefore, the orthosis may be worn to provide temporary protection for the deficient collateral ligaments as they heal from injury or surgery, or as a more permanent back-up for collateral ligaments that are irreparably damaged or deficient, or even as a functional substitution in a case where the patient's collateral ligaments are totally inoperative.

Referring to FIGS. 4A and 4B, it will be observed that the leading lower edge of stop 50 engages the upper surface of tibial member 31 when the joint is fully extended. Under such circumstances, the stop 50 simply functions as a reinforcement against possible hyperextension, performing the same function previously described in connection with protuberance 41 and recess 40. However, in some instances even full extension as shown in these figures is to be avoided during a period of treatment or recovery, in which case an orthopedic specialist may shift stop 50 downwardly sightly and lock it in its adjusted position by screws 51, so that the lower end of the stop will engage the tibial member 31 just before full extension occurs. The distance which stop 50 is lowered depends, of course, upon the patient's condition and the treatment required and, subject to those considerations, periodic readjustment of the stop in an upward direction may be deemed desirable over the term of recovery. Thus, injured ligaments may be allowed to assume a progressively greater role in preventing hyperextension as the healing process continues.

FIGS. 8–12B show a joint assembly 13' that is identical to the assembly of FIGS. 3–7B except for differences in the recesses, their cam surfaces or tracks, and the protuberances which engage those tracks. The orthotic joint of FIG. 8 is intended for a patient with a damaged or deficient posterior cruciate ligament, the other knee ligaments being operative and not requiring protective treatment. A primary function of the posterior cruciate ligament is to draw the femur in a posterior direction during flexion and to restrain it in a posterior location when the knee is so flexed. The orthotic joint 13' mimics the function of a normal posterior cruciate ligament in that respect without assuming functions performed by other ligaments such as, for example, the collateral ligaments. Thus, it will be evident from FIGS. 10A, 10B, 11A, and 11B that slight upward movement of femoral member 30 with respect to tibial member 31 will be possible without any restraining action by the orthotic joint, the extent of such movement being indicated in these figures by phantom lines. Such relative upward movement of the femur in the natural joint is prevented by collateral ligaments and, since it is assumed that the patient's collateral ligaments are healthy and operative, the orthotic joint 13' does not interfere with the normal action of those collateral ligaments.

The sizes, positions, and shapes of recesses 40' and 43' differ from those of recesses 40 and 43. Also, there are only two protuberances 42', 44' rather than three, and their locations differ from those of protuberances 42, 44. When the leg is fully extended, protuberance 42' and the peripheral cam track of recess 40' are not operative (while protuberance 42 is shown in FIG. 9A in contact with the lower track of recess 40', the head portion of femur 34 is already fully seated within its socket); however, the peripheral cam track of recess 43' cooperates with protuberance 44' to prevent relative upward displacement of the femoral head portion 34 with respect to tibial member 31. As the femoral member 30 swings into a flexed condition (FIGS. 10A–11B), protuberance 42' rides forwardly (anteriorly) and upwardly (proximally) along the arcuate lower cam track of recess 40' to urge the femoral head portion 34 rearwardly (posteriorly). During such flexion, protuberance 44' and the cam track of recess 43' are generally inoperative; however, in a state of maximum flexion, both of the protuberances 42', 44' engage the cam tracks of their respective recesses 40', 43' to prevent upward movement of the femoral head portion 34 within socket 36.

FIGS. 13–16B show an orthotic joint 13" which is the same as previously-disclosed joints 13 and 13' except for further variations in the sizes, shapes, and locations of the recesses 40', 43" and the number and positions of protuberances 41", 42", and 44". Joint assembly 13" would be used in an orthosis for a patient having an injured or deficient anterior cruciate ligament. That ligament normally urges the head of the femur of the knee joint forwardly (anteriorly) as the leg is extended. Therefore, as the orthotic joint shifts between a position of 90° flexion, to 45° flexion, and then to extension, the cam surfaces of the recesses and the protuberances that serve as cam riders urge the head portion 34 in an anterior direction without at the same time constraining or interfering with the action of the patient's knee joint ligaments except for the anterior cruciate ligament.

At 90°, protuberance 42" engages the cam track of recess 43" to limit rearward (posterior) displacement of the head of femoral member 30 within its socket 36 (FIG. 14B). As extension continues, protuberance 44" becomes operative to direct the femoral head portion forwardly (anteriorly) (FIG. 15B) and, finally, when full extension is achieved, protuberance 41" coacts with the peripheral cam track of recess 40" to hold the head portion in its forward (anterior) position (FIG. 16A).

In each construction, the protuberances function as cam riders and coact with the narrow cam surfaces or tracks of the recesses to prevent abnormal movements of the knee where the ligament group that normally functions to prevent such abnormal movements is lacking or deficient. At the same time, the orthotic joint does not interfere with the functioning of normal or healthy ligaments of the patient's knee. To achieve such stability while at the same time providing the desired laxity in the operation of the joint, more than one area of cam action is believed necessary. Where there is more than a single protuberance along one side of the femoral head portion, those protuberances might of course be joined into a single protuberance having plural zones of sequential contact with the associated cam surface or track. While it is believed important to have two cam-providing recesses to achieve the multiple functions required, it is also believed apparent that the arrangement of cam recesses and protuberances or projections might be reversed, so that what is shown on the medial side of the femoral head portion might be located on the lateral side, and vice versa, and further, that the projections or protuberances might instead be provided by the walls of the socket with such protuberances then extending into cam-defining recesses formed in opposite sides of the femoral head portion.

While in the foregoing, embodiments of the invention have been disclosed in considerable detail for purposes of illustration, it will be understood by those skilled in the art that such details may be varied without departing from the spirit and scope of the invention.

I claim:

1. An orthotic knee joint assembly comprising a rigid planar femoral member having a head portion with a narrow arcuate bearing surface of varying radii of curvature and having a femoral sidebar projecting from said head portion and adapted to extend upwardly alongside a wearer's upper leg; a rigid tibial member having a body portion and a tibial sidebar adapted to extend downwardly alongside a wearer's lower leg; said body portion having a pair of planar side walls spaced apart to define a narrow upwardly-opening socket slidably receiving said head portion and having an arcuate guide surface engagable with said bearing surface for guiding movement of said members between flexion and extension along constantly changing instantaneous axes of rotation; said bearing surface being slidable posteriorly and anteriorly along said guide surface when said members are in flexion; and means provided by said members to direct said bearing surface with respect to said guide surface during articulation of a patient's knee; wherein the improvement comprises said head portion having planar surfaces on opposite sides thereof slidably engaging said side walls of said body portion within said socket, whereby, on each side of said head portion are presented a pair of opposing and slidably engaging surfaces, one provided by said head portion and the other by said body portion; one of said opposing surfaces of one of said pairs being provided with a recess having its major dimensions extending in the plane of such surface and having a narrow cam track about the periphery thereof; and the other of said opposing surfaces being provided with a plurality of protuberances engagable with portions of said cam track during flexion and extension for exerting constraining forces similar to those that would be exerted by certain ligaments of the wearer's knee if such ligaments were present, healthy, and functioning properly; said recess being substantially larger than said protuberances so that at any given stage of articulation the contact between a protuberance and said cam track constrains movement of said head portion in only certain selected directions along a plane parallel with said side walls without constraining movement of said head portion in directions along said plane opposite from said selected directions; said protuberances being positioned and arranged for successively engaging portions of said cam track of said recess during flexion and extension with only one of said protuberances engaging said track at any given stage of articulation.

2. An orthotic knee joint assembly comprising a rigid planar femoral member having a head portion with a narrow arcuate bearing surface of varying radii of curvature and having a femoral sidebar projecting from said head portion and adapted to extend upwardly alongside a wearer's upper leg; a rigid tibial member having a body portion and a tibial sidebar adapted to extend downwardly alongside a wearer's lower leg; said body portion having a pair of planar side walls spaced apart to define a narrow upwardly-opening socket slidably receiving said head portion and having an arcuate guide surface engagable with said bearing surface for guiding movement of said members between flexion and extension along constantly changing instantaneous axes of rotation; said bearing surface being slidable posteriorly and anteriorly along said guide surface when said members are in flexion; and means provided by said members to direct said bearing surface with respect to said guide surface during articulation of a patient's knee; wherein the improvement comprises said head portion having planar surfaces on opposite sides thereof slidably engaging said side walls of said body portion within said socket, whereby, on each side of said head portion are presented a pair of opposing and slidably engaging surfaces, one provided by said head portion and the other by said body portion; one of said opposing surfaces of one of said pairs being provided with a recess having its major dimensions extending in the plane of such surface and having a narrow cam track about the periphery thereof; and the other of said opposing surfaces being provided with at least one protuberance engagable with portions of said cam track during flexion and extension for exerting straining forces similar to those that would be exerted by certain ligaments of the wearer's knee if such ligaments were present, healthy, and functioning properly; said recess being substantially larger than said protuberance so that at any given stage of articulation the contact between said protuberance and said cam track constrains movement of said head portion in only certain selected directions along a plane parallel with said side walls without constraining movement of said head portion in directions along said plane opposite from said selected directions; one of said opposing surfaces of the other of said pairs being provided with a second recess having its major dimension extending in the plane of such surface and having a second narrow cam track about the periphery thereof; and the other of said opposing surfaces of said other pair being provided with at least one second protuberance engagable with portions of said second cam track during flexion and extension for exerting constraining forces similar to those that would be exerted by selected ligaments of the wearer's knee if such ligaments were present, healthy, and functioning properly; said second recess being substantially larger than said second protuberance so that at any given stage of articulation the contact between said second protuberance and said second cam track contrains movement of said head portion in only certain selected directions along a plane parallel with said side walls without constraining movement of said head portion in directions along said plane opposite from said selected directions; said first and second protuberances being positioned and arranged for successively engaging their respective cam tracks so that only one of said protuberances is engagable with its cam track at any given intermediate stage of articulation between full extension and flexion.

3. The assembly of claim 2, in which stop means are provided along the anterior of said femoral sidebar adjacent said head portion; said stop means being engagable with the anterior of said body portion for limiting the degree of maximum extension of said joint assembly.

4. The assembly of claim 3 in which said stop means is adjustable along said femoral sidebar for engaging and stopping said body portion at any of a multiplicity of angular positions of said tibial member relative to said femoral member and thereby selectively varying the angular degree of maximum extension of said joint assembly.

5. The assembly of claim 4 in which said stop means comprises a member of U-shaped cross section engaging the lateral, medial, and anterior surfaces of said femoral sidebar; and locking means for anchoring said U-shaped member in selected positions of adjustment along said femoral sidebar.

6. The assembly of claim 3 in which said assembly is a component of a complete knee orthosis; said orthosis including a second assembly similar to said first-mentioned assembly; means for securing said femoral sidebars along opposite sides of a patient's upper leg; and means for securing the tibial sidebars along opposite sides of a patient's lower leg.

7. The assembly of claim 2, in which said assembly is a component of a complete knee orthosis; said orthosis including a second assembly similar to said first-mentioned assembly; means for securing said femoral sidebars along opposite sides of a patient's upper leg; and means for securing the tibial sidebars along opposite sides of a patient's lower leg.

* * * * *